(12) United States Patent
Ionescu et al.

(10) Patent No.: US 12,411,134 B2
(45) Date of Patent: Sep. 9, 2025

(54) APPARATUS AND METHOD FOR MEASURING HORMONE CONCENTRATION IN BIOFLUIDS

(71) Applicant: ECOLE POLYTECHNIQUE FEDERALE DE LAUSANNE (EPFL), Lausanne (CH)

(72) Inventors: Mihai Adrian Ionescu, Ecublens (CH); Sheibani Shokoofeh, St-Sulpice (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 880 days.

(21) Appl. No.: 17/539,730

(22) Filed: Dec. 1, 2021

(65) Prior Publication Data
US 2022/0170920 A1 Jun. 2, 2022

(30) Foreign Application Priority Data

Dec. 2, 2020 (EP) .................................. 20211196

(51) Int. Cl.
*G01N 33/543* (2006.01)
*H10D 64/27* (2025.01)

(52) U.S. Cl.
CPC ....... *G01N 33/5438* (2013.01); *H10D 64/519* (2025.01)

(58) Field of Classification Search
CPC .......... A61B 2562/125; A61B 5/14507; A61B 5/14546; A61B 5/1468; G01N 27/4145; G01N 33/5438; H01L 29/4238
See application file for complete search history.

(56) References Cited

U.S. PATENT DOCUMENTS

2017/0089899 A1* 3/2017 Kundrod .......... G01N 33/56988
2019/0110722 A1* 4/2019 Ionescu .............. A61B 5/14517
(Continued)

FOREIGN PATENT DOCUMENTS

WO  2019/044993 A1  3/2019
WO  2019/051471 A1  3/2019
(Continued)

OTHER PUBLICATIONS

Espacenet English Translation of WO2019044993. (Year: 2019).*
(Continued)

*Primary Examiner* — Kathryn Elizabeth Limbaugh
(74) *Attorney, Agent, or Firm* — Maschoff Brennan

(57) ABSTRACT

One embodiment of the present invention concerns a biosensor for sensing stress hormone cortisol concentration in a biofluid. The biosensor comprises: an electrical transistor transducer comprising a transistor gate electrode; a sensing electrode element comprising a metal element having a biofluid facing surface, and a graphene layer on the biofluid facing surface of the metal element, the sensing electrode element being connected to the transistor gate electrode by an electrical connector to form an extended gate configuration with the transistor gate electrode; and a reference electrode configured to be in contact with the biofluid, and configured to electrically bias the transistor gate electrode through the biofluid. The sensing electrode element is functionalised by at least a layer of aptamers placed indirectly or directly on the graphene layer, and configured to catch cortisol hormones in the biofluid to thereby change a surface potential of the sensing electrode element.

18 Claims, 5 Drawing Sheets

(56) References Cited

U.S. PATENT DOCUMENTS

2019/0223795 A1 7/2019 Patolsky et al.
2019/0376926 A1 12/2019 Tarasov

FOREIGN PATENT DOCUMENTS

| WO | 2019/244113 A1 | 12/2019 |
| WO | 2020/0217996 A1 | 10/2020 |

OTHER PUBLICATIONS

Hao et al., Modulating the Linker Immobilization Density on Aptameric Graphene Field Effect Transistors Using an Electric Field, May 7, 2020, American Chemical Society, vol. 5, p. 2503-2513. (Year: 2020).*

Hao et al., Supporting Information, May 7, 2020, American Chemical Society, p. 1-6. (Year: 2020).*

Kyung-Mi Song et al., "Aptamers and Their Biological Applications" Sensors, vol. 12, No. 12, Jan. 9, 2012, pp. 612-631.

Hao Zhuang et al., "Modulating the Linker Immobilization Density on Aptameric Graphene Field Effect Transistors Using an Electric Field", ACS Sensros, vol. 5, No. 8, Aug. 28, 2020, pp. 2503-2513.

Woo Kyoungmin et al., "Enhancement of cortisol measurement sensitivity by laser illumination for AlGaN/GaN transistor biosensor" Biosensors and Bioelectronics, vol. 159, Apr. 12, 2020, p. 112186.

Bankim J. Sanghavi et al., "Aptamer-funcationalized nanoparticles for surface immobilization-free electrochemical detection of cortisol in a microfluidic device" Biosensors and Bioelectronics, vol. 78, Nov. 28, 2015, pp. 244-252.

EP Search Report in Application No. 20211196.9 dated May 12, 2021.

* cited by examiner

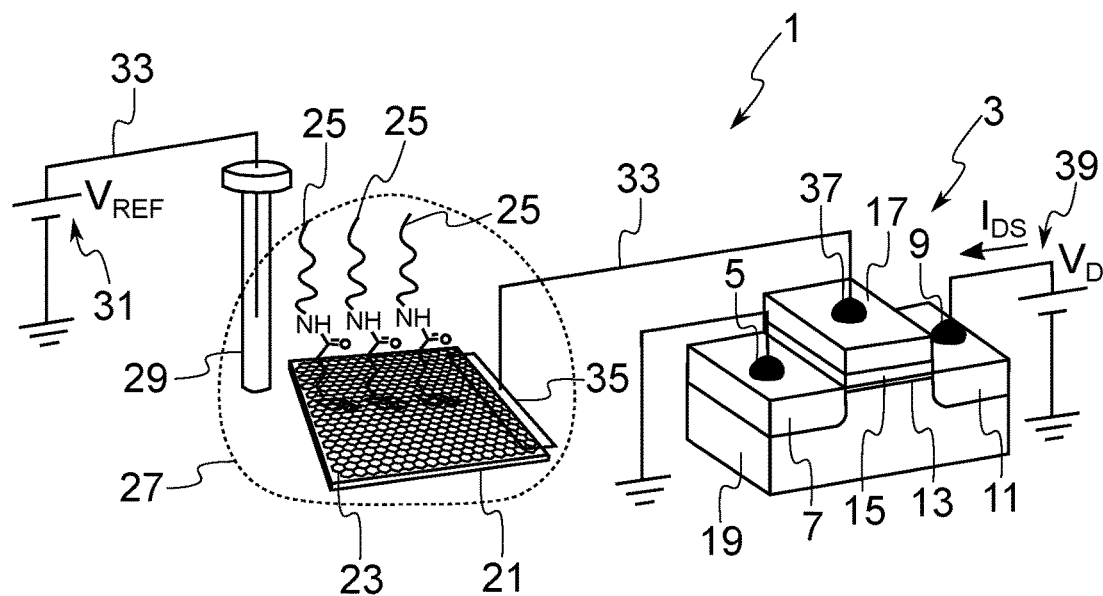
Fig. 1
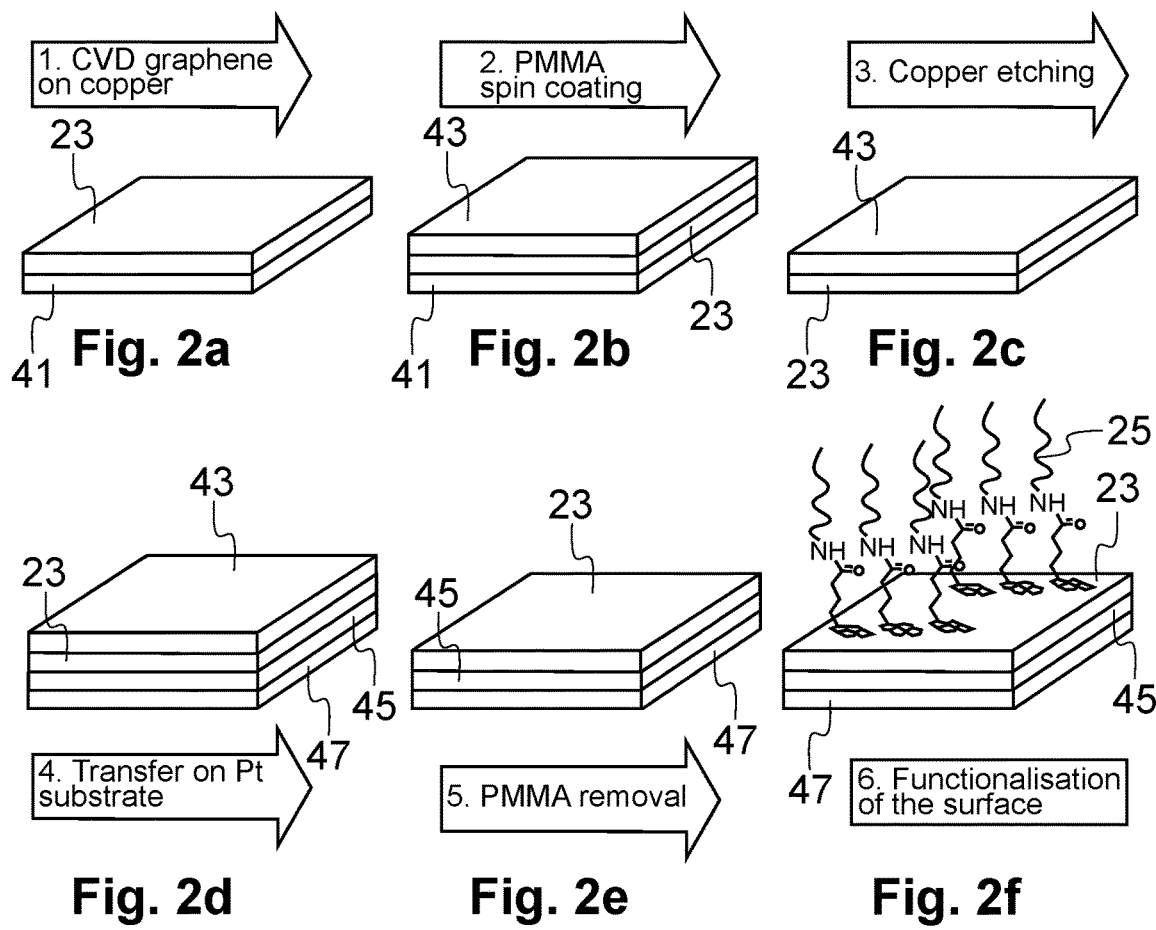
Fig. 2a  Fig. 2b  Fig. 2c
Fig. 2d  Fig. 2e  Fig. 2f

APPARATUS AND METHOD FOR MEASURING HORMONE CONCENTRATION IN BIOFLUIDS

TECHNICAL FIELD

The present invention relates to a sensor apparatus that may be used to sense the concentration of the hormone of stress, cortisol, in human biofluids, such as blood, sweat, interstitial fluids, saliva, tears and urine. More specifically, the apparatus is based on an electrode with a layer of graphene decorated with aptamers that is electrically connected to the gate of a semiconductor device. A change in the concentration of cortisol in the biofluid is mirrored in a change of the current of the semiconductor device. The invention also relates to a corresponding sensing method and to a method of fabricating the sensor apparatus.

BACKGROUND OF THE INVENTION

Continuous and specific detection of cortisol is pivotal in the fight against chronic stress disorders. Obesity, type two diabetes, heart diseases, anxiety, and depression are just few examples of medical conditions strictly related to stress. Cortisol secretion by the adrenal gland cortex has been demonstrated to be highly unstable during psychological or physical tension, and its circadian rhythm is strongly influenced under unsustainable stress. Over the last few years, biosensors based on electrical detection have attracted a lot of attention, due to the possibility of implementing efficient label-free detection mechanisms. Among them, the field-effect transistors (FETs) are the best candidates, because they can be easily integrated in well-known electronic designs. Innovative structures, such as nanowires and nanoribbons, have been proposed as transducers to improve the insufficient detection sensitivity of classical metal-oxide-semiconductor field-effect transistors (MOSFETs) employed as biosensors. However, the main problems with these devices are the unestablished process flow for mass production, and the difficulty in interfacing them with read-out circuits for wearable systems.

In recent years, ion-sensitive field-effect transistors (ISFETs) have attracted a lot of attention thanks to their fast response, sensitivity, low power consumption, ability to offer co-integrated readouts and full on-chip circuit design, miniaturisation and low cost. All these features make them one of the most promising candidates for wearable systems. ISFETs form a subset of potentiometric sensors that are not affected by signal distortions arising from the environment, thanks to the input gate potential that is connected to the electrical FET transducer. They are capable of converting any little variation of the electrical charge placed in the vicinity of the transistor gate, such as any species carrying charge (similarly to ions), and this variation becomes detectable by a variation of the FET drain current. The operation of an ISFET sensor is based on the dependence of the threshold voltage of a MOSFET on the gate work function, which can be modulated by the charge of an ion-sensitive membrane. As state-of-the-art nano-MOSFETs operate at low voltage with low currents, ISFETs inherit their high charge sensitivity. Any chemical reactions at the top of the gate dielectric with the various species existing in the solution may induce a change of gate stack electrical characteristics. Therefore, the current-voltage characteristic of the ISFET sensor can be modulated if the gate dielectric is exposed to interactions with fluids. However, in an advanced complementary metal-oxide-semiconductor (CMOS) process, the gate stack is part of the so-called front-end-of-line (FEOL) process that is highly standardised and cannot be easily modified or functionalised for sensing. To address this issue, extended-gate field-effect transistors (EGFETs) have been proposed for sensing applications. In such a sensor architecture, the base transducer is a standard nano-MOSFET while the sensing element is formed by a specific functional layer on the extension of the metal gate that can be an external electrode or a metal layer fabricated in the back-end-of-line (BEOL) process, and connected to the nano-MOSFET gate. The EGFET configuration has major advantages thanks to the separation of the integrated transducing element from the functional layers, including higher stability, less drift and even less temperature sensitivity. Few research groups have attempted to design cortisol sensors exploiting FET devices, but these solutions fail to fulfil the sensitivity and selectivity performance requirements needed when sensing human biofluids.

One of the challenges of the FET-based sensors is the Debye screening effect in ionic liquids that prevents its electrical potential to extend further than a certain distance, known as Debye length ($\lambda_D$). In other words, the Debye length is a measure of a charge carrier's net electrostatic effect in a solution and how far its electrostatic effect persists. The value of $\lambda_D$ depends on the ionic strength of the liquid. For instance, $\lambda_D$ in phosphate-buffered saline (1× PBS), which is commonly used in biological research, is less than 1 nm. The physical lengths of antibody-antigen complexes, usually utilised for ISFET biosensors, are greater than $\lambda_D$ associated with physiological media. Therefore, the challenge for designing a FET sensor for detection of the cortisol is the choice of an appropriate catch probe overcoming the Debye length. As cortisol is charge-neutral, the electrical recognition of the cortisol is subject to the use of an electrically active mediator catch probes that have their own charge to modulate the gate potential within the detectable Debye length. Thus, the binding between the catch probe and the cortisol will cause a change in the total gate potential, and consequently in the measured drain current. Until now different capturing probes including e.g. molecularly sensitive polymers and antibodies have been used in the reported ISFET devices for detection of the cortisol. However, these types of capturing probes have the disadvantage that it is difficult to synthesise them in vitro, and thus they have a relatively high batch-to-batch difference. Furthermore, it is difficult to design them for different degrees of affinity for a targeted molecule versus a modified disturbing analogue. Moreover, they are strongly affected by temperature fluctuations, and are instable for long term storage.

SUMMARY OF THE INVENTION

It is an object of the present invention to overcome at least some of the problems identified above related to sensing cortisol in human biofluids, and in particular related to sensing the cortisol stress hormone when using EGFET-based sensors. Similar methods and FET device principles as the ones proposed here can be used to sense other hormones in biofluids, by changing the type of used aptamers in the proposed graphene-based electrode. All these types of sensors can be considered as being label-free, proving solutions for real-time quasi-continuous measurements of hormone concentrations in sweat.

According to a first aspect of the invention, there is provided a biosensor for sensing cortisol concentration in human biofluids as recited in claim 1.

The present invention thus proposes a cortisol biosensor comprising a transistor-based transducer, which may be a standard CMOS for example, such as a standard 0.18 µM CMOS transistor, whose gate is externally extended with a sensing electrode, which may comprise a platinum element, and on which an atomically thin layer of graphene has been transferred. The graphene layer is in turn decorated with aptamers, such as 61-nuclotide-based aptamers. The combined use of a thin graphene layer, and the aptamers, and in particular the 61-nuclotide-based aptamers, as catching probes or sites allow the enhancement of the sensor response in a concentration range (1 nM-10 µM) wider than the biological one of the human circadian rhythm (83 nM-0.69 µM). The graphene layer offers surface dimensions comparable with the analyte dimensions, and the short enough probes allows the Debye screening provided by the ionic double layer generated on every charged surface immerged in an ionic solution to be overcome. Furthermore, the proposed cortisol sensor based on a simple EGFET configuration has the possibility to be fully integrated in a low-power wearable system. The proposed sensor also has the advantages of having a low limit of detection (LOD), extended linear range, high sensitivity, negligible drift and low hysteresis. Moreover, the invention proposes a first of its kind predictive unified calibrated model for hormone sensing with FETs, capable of predicting the sensor response in all the working regimes with high accuracy, using both FET-specific electrical and sensor-specific concentration parameters. A hormone is understood to mean any member of a class of signalling molecules, produced by glands in multicellular organisms. The sensor according to the present invention can be used for both point-of-care single shot measurements, as well as for continuous measurements in wearable systems.

According to a second aspect of the invention, there is provided a wearable sensor-on-chip comprising the biosensor according to the first aspect of the present invention.

According to a third aspect of the invention, there is provided a method of fabricating a biosensor.

Other aspects of the invention are recited in the dependent claims attached hereto.

BRIEF DESCRIPTION OF THE DRAWINGS

Other features and advantages of the invention will become apparent from the following description of non-limiting example embodiments, with reference to the appended drawings, in which:

FIG. 1 shows schematically a biosensor in a system-in-package configuration according to a first example embodiment of the present invention, and comprising an extended gate configuration;

FIGS. 2a to 2f illustrate the fabrication steps of transferring a graphene layer onto the sensing electrode and the step of functionalising it;

DETAILED DESCRIPTION OF EMBODIMENTS OF THE INVENTION

Figure 3:
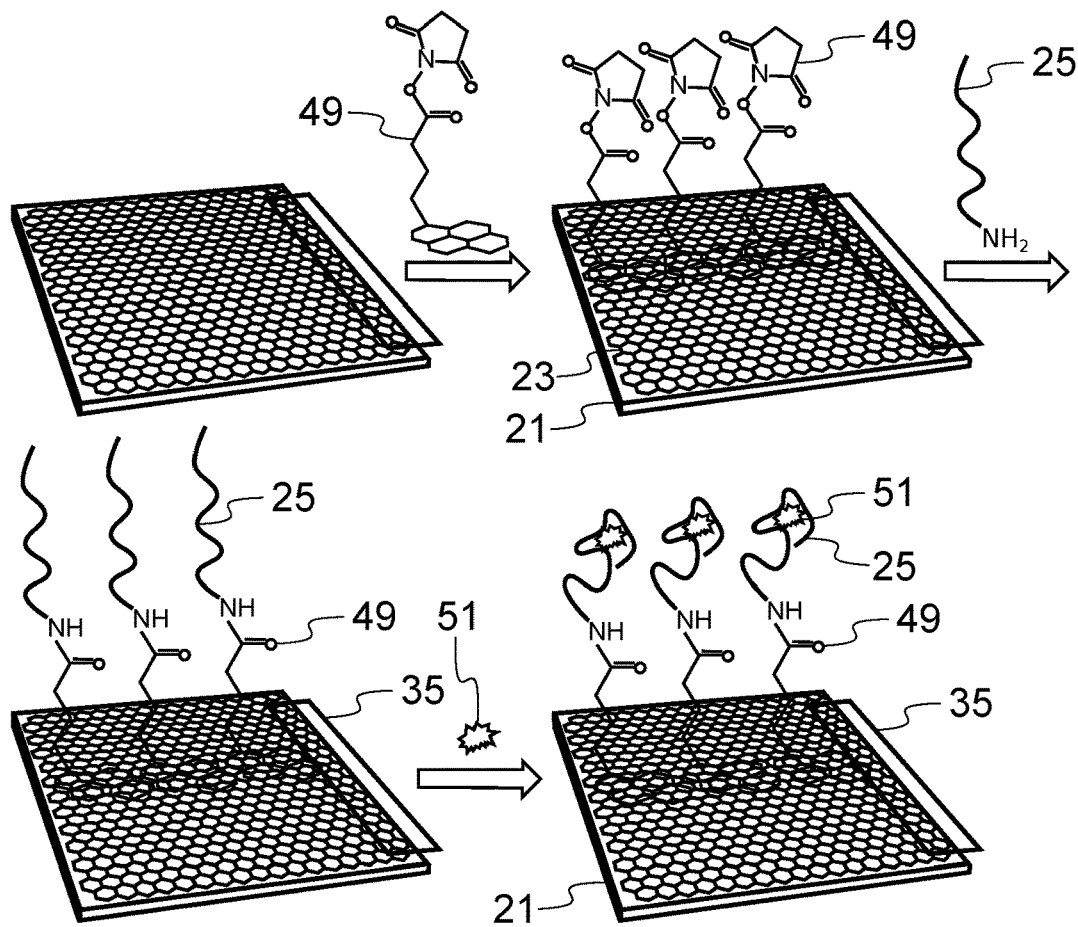
FIG. 3 illustrates in more detail the step of functionalising the sensing electrode.

Some embodiments of the present invention will now be described in detail with reference to the attached figures. The different embodiments are described in the context of measuring or sensing cortisol levels in human body fluids, but the teachings of the invention are not limited to this environment. Identical or corresponding functional and structural elements which appear in the different drawings are assigned the same reference numerals. As utilised herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z." Furthermore, the term "comprise" is used herein as an open-ended term. This means that the object encompasses all the elements listed, but may also include additional, unnamed elements. Thus, the word "comprise" is interpreted by the broader meaning "include", "contain" or "comprehend".

The present example embodiment demonstrates a label-free cortisol detection method and a related apparatus with an extended-gate field-effect transistor (EGFET), which overcomes the Debye screening limitation for charge sensing by using aptamer-decorated, and in particular 61-base-pair aptamer-decorated single-layer graphene on platinum as a gate electrode. The proposed solution is a label-free sensing method because no label is attached to the substance to be sensed, which is thus sensed without modifying it. It is to be noted that the present embodiment comprises a platinum element as part of the sensing electrode or element, but any other noble metal element could be used instead. In chemistry, noble metals are understood to be metallic elements that show outstanding resistance to chemical attack even at high temperatures. They are well known for their catalytic properties and associated capacity to facilitate or control the rates of chemical reactions. In the present description noble metals comprises ruthenium (Ru), rhodium (Rh), palladium (Pd), osmium (Os), iridium (Ir), platinum (Pt), gold (Au), copper (Cu), silver (Ag), rhenium (Re), and mercury (Hg). The sensing element is physically separated from the electrical transducer, enabling the possibility to implement the sensor in a three-dimensional (3D) configuration, with a nano-MOSFET as a base voltametric transducer, and the sensing electrode fabricated in the BEOL of a CMOS process, resulting in a low power wearable sensory electronic chip. The use of atomically thin graphene is particularly advantageous to chemically bind the aptamers and bring the recognition event of the analytes within the Debye limit of detection, with high sensitivity.

FIG. 1 schematically illustrates the sensing apparatus 1, device or system, also referred to simply as a sensor or biosensor. A transistor-based transducer 3 is used to determine the characteristics of the transistor, and more specifically the $I_{DS}$-$V_G$ responses, to deduce the cortisol concentration in the liquid to be sensed, where $I_{DS}$ is the transistor drain current, i.e. the drain to source current, and $V_G$ is the gate voltage. In this example, the transducer is a MOSFET, such as a nano-MOSFET, and in particular an 18 μm MOSFET. In the transistor, a conductive channel, also known as a FET channel, can be formed between a source element, node, terminal or region and a drain element, node, terminal or region to allow current, referred to as drain current, to flow in the channel. The source element, referred to also as a source, in this example comprises a source electrode or electrical contact 5 in direct contact with a source doped region 7, while the drain element, referred to also as a drain, comprises a drain electrode or electrical contact 9 in direct contact with a drain doped region 11. These two doped regions are of the same type, namely either of n or p type. The conductive channel can be formed in a channel element 13 with adjustable conductivity between the source and drain doped regions in the present example. In this example, the channel element is a thin or ultra-thin silicon (Si) body (in this example with a thickness smaller than 50 nm). An insulator 15 or a dielectric layer is placed between the channel element 13 and a gate electrode 17, i.e. a conductive element, such as a metal layer or plate. The gate electrode and the insulator are both part of the gate stack or gate element. The insulator is in this example on the channel element. A substrate 19, referred to also as a base silicon, is also provided, and is in this example in direct contact with the first and second doped regions 7, 11 and the channel element 13. The first and second doped regions 7, 11, the channel element 13 and the substrate 19 are in this example of silicon with possibly different doping levels. Furthermore, in this example, the first and second doped regions are of n type, while the substrate is of p type, or vice versa.

As is shown in FIG. 1, the gate is extended through an external electrically connected electrode 21, which in this specific example is a platinum Pt electrode or platinum on glass electrode, which is properly functionalised with a monolayer graphene sheet 23, decorated with selected aptamers 25 to address the detection of the cortisol within the Debye length. Graphene is understood as an allotrope of carbon consisting of a single layer of atoms arranged in a two-dimensional honeycomb lattice. The graphene sheet and the aptamers thus collectively form a functionalisation layer deposited on top of the electrode 21. The functionalisation layer is arranged to be in contact with the solution (a fluid) 27 with a given cortisol concentration. Thus, the graphene sheet 23 is disposed on the fluid facing surface of the electrode 21. The electrode 21 together with at least a portion of the functionalisation layer is understood to form a sensing electrode element. The functionalisation layer, also known as a sensor or probe material layer, is used for selective detection of the properties of the analytes of interest (in this case cortisol hormones). The platinum/graphene electrode 21 is exposed to, or immersed in a liquid solution 27, where a reference electrode 29, such as a standard Ag/AgCl or fluorinated graphene reference electrode, may be used to electrically bias the gate of the MOSFET 3 through the solution 27. The sensing gate stack may be defined to comprise at least the solution 27, the reference electrode 29 and the functionalisation layer.

The sensor 1 also comprises an input bias source 31, which in this example is a voltage source. The voltage value across the bias voltage source 31 is denoted by $V_{REF}$. The input bias source is configured to apply a static DC voltage signal to the solution 27 under test that is placed between the reference electrode 29 and the functionalised graphene electrode 21. It is to be noted that the word "signal" is used in the present description in its broad sense and does not imply that any information would be coded in the signal. The applied signal here has a constant signal level but it can be tuned to different values to place the FET 3 in the most convenient operation point from the point of view of signal-to-noise ratio and the power consumption. However, other voltage signals may be applied instead if one wants to drive the sensing element into other regimes of operation. These signals may have the waveform of a sawtooth wave, a sine wave (sinusoid), a triangle wave, etc. The bias voltage source is connected to the reference electrode 29 by an electrical connector 33. The reference electrode 29 may be considered to be an electrically conductive element, optionally a substantially flat plate, such as a metal plate, in which a reversible chemical reaction can happen at the surface to maintain the interface potential with the liquid. This electrode is usually immersed in a chlorine-saturated solution in order to stabilise its potential for all pH values and to avoid dechlorination of the surface. It is to be noted that in the present description the notation "reference electrode" also covers any type of integrated miniaturised reference electrode or an integrated miniaturised quasi-reference electrode, as well as a simple metal electrode immersed in the solution. The bias voltage source 31 is arranged to electrically bias the reference electrode 29 and thereby to set an electric potential of the solution. Thus, the reference electrode 29 is used to bias the solution. The reference electrode 29 together with the solution 27 and the functionalised sensing electrode 21 together form a liquid gate.

An electrical contact pad 35 is provided on the sensing electrode 21, and which is coupled via another electrical connector 33 to a gate electrical contact 37. In the example configuration of FIG. 1, the source electrical contact 5 is grounded, while the drain electrical contact 9 is connected to another voltage source 39 to electrically bias the source element.

Experiments have been carried out with a reference buffer and solutions with various known cortisol concentrations. Following cortisol catching, the resulting changes in the MOSFET drain current are recorded and analysed. It is to be noted that in principle the drain electrode 9 can be biased by the voltage source 39, as shown in FIG. 1, and in this case the current $I_{DS}$ is monitored (also shown in FIG. 1), or can it be biased by a constant current source, and in this case the change of the drain voltage would be monitored. The significant advantage of this proposed configuration relies on using any stable and reproducible standard CMOS technology node (data reported here are for a 0.18 μm CMOS) for the FET transistor as a transducer, while separately functionalising the extended electrode that is connected to the transistor gate. This configuration results in the possibility of obtaining a fully 3D lab-on-chip sensory system with the active detecting element being fabricated in the BEOL process, i.e. the specific Pt/graphene/aptamer layer, and the reference electrode (e.g. another fluorinated metal/graphene electrode) in the BEOL of the CMOS process. Such a 3D chip is compatible with the recently proposed concept of lab-on-skin (LoS) suitable for collection and analysing the concentrations of biomarkers in human sweat, for instance. As described later with reference to FIGS. 6 to 9, such a conceptual LoS system includes an integrated microfluidic system, such as an SU-8 photoresist integrated microfluidic system, that allows the liquid under test (LUT) to flow over both the planar chlorinated reference electrode and the graphene/aptamer sheet.

The transfer process of the graphene 23 onto the sensing electrode 21 is next described in more detail with reference to FIGS. 2a to 2f. First, as shown in FIG. 2a, a graphene film or layer 23 is deposited on a substrate 41, which in this example is a copper substrate. The deposition is in this example carried out by chemical vapor deposition (CVP). Then, as shown in FIG. 2b, a thin layer of poly(methyl methacrylate) (PMMA) 43, which is a transparent thermoplastic, and more specifically acrylic or acrylic glass, is coated, and more specifically spin-coated, onto the as grown graphene film 23 on the substrate followed by a baking process and the etching of the substrate 41 by for example an ammonium persulfate 0.1 M solution as shown in FIG. 2c. The floated polymer/graphene is rinsed with DI water several times and then fished out onto the platinum plate 45, which is on top of a glass layer 47, and thus collectively forming an extended gate (or at least part of it) as shown in FIG. 2d. Next, and as shown in FIG. 2e, the polymer (i.e. the PMMA layer) is dissolved for example with acetone and rinsed with isopropyl alcohol (IPA), for example. After the transfer process, the prepared electrode 21 is functionalised with aptamers 25 as shown in FIG. 2f. By inspecting the transferred graphene on platinum before and after aptamers functionalisation, the uniformity and cleanness of the transferred graphene onto the Pt electrode 21 and of the functionalisation of graphene with aptamers can be confirmed. Moreover, there are no defects and cracks on the graphene 23 after the functionalisation process.

Figure 4:
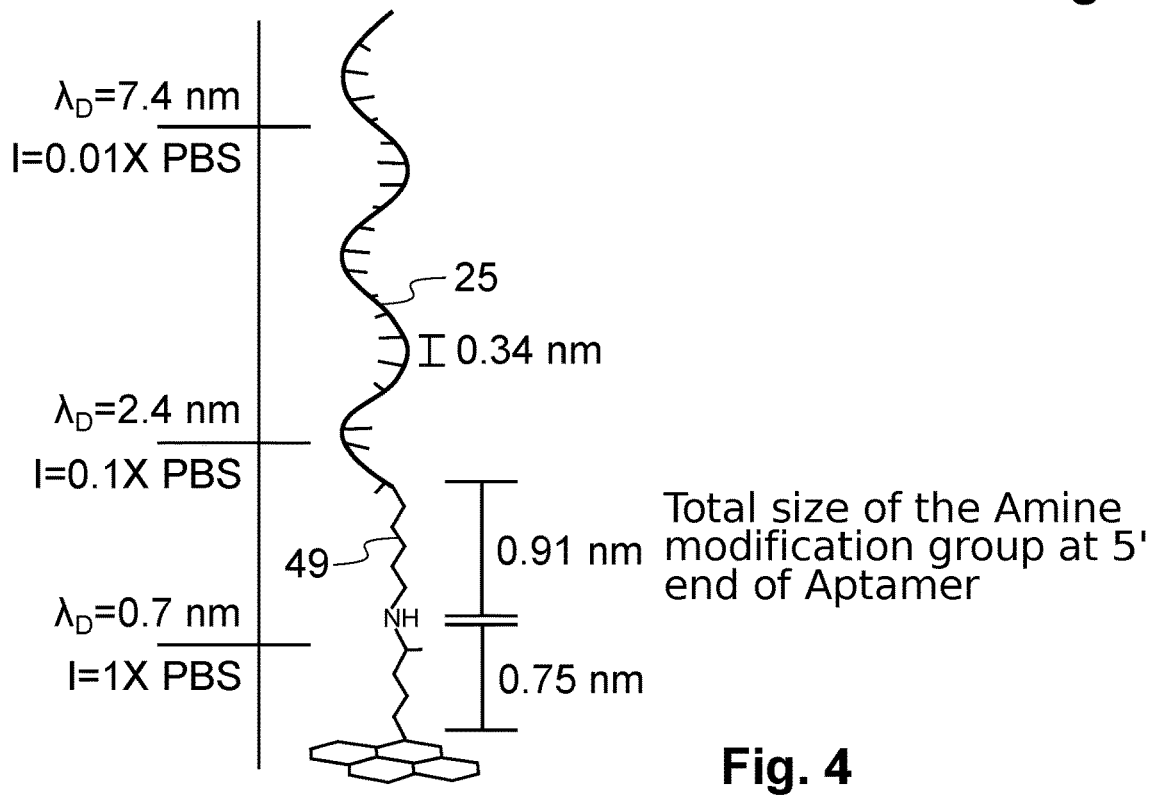
FIG. 4 illustrates the nano-scale thickness of the functionalisation layer.

The chemistry and the different steps for the electrode modification as well as the following attachment of the targets are next explained in more detail with reference to FIG. 3. To efficiently functionalise the electrode, linker molecules 49 are used to connect or attach the aptamers to the graphene 23. In this example, 1-Pyrenebutyric acid N-hydroxysuccinimide ester (PBSE) with a thickness of 0.75 nm is used as the linker molecule between the aptamers 25 and the graphene sheet 23. Furthermore, in this specific example, the PBSE molecules have a thickness or length of 0.75 nm or approximately 0.75 nm. The PBSE molecules 49 can attach to the graphene surface by their carbon rings via π-π interactions. Moreover, the length of the amine group, which is added at the 5' end of the aptamer to enable it for the EDS-NHS reaction with the PBSE molecules, is in this example 0.91 nm. Therefore, the total distance between the aptamer and the graphene surface (and more specifically the distance between the distal end of the amine group and the graphene surface) is 1.66 nm as also illustrated in FIG. 4. It is to be noted that the aptamer sequence used in the present example is 5'-amine-AG CAG CAC AGA GGT CAGATG CAA ACC ACA CCT GAG TGG TTAGCG TAT GTC ATT TAC GGACC. The proposed method and apparatus can be used for other aptamer sequences as well that could have specific catch feature for other types of hormones. Considering the fact that the Debye length in a physiological salt environment (1× PBS), diluted 0.1× PBS, and 0.01× PBS are approximately 0.7 nm, 2.4 nm, and 7.4 nm, respectively, the Debye length in 0.05× PBS, which is used in the present example as the solution for taking the measurement of the response of the sensor 1, should be between 2.4 nm and 7.4 nm. Therefore, this method allows us to retain the catch probe aptamers 25 close to the conductive surface, and the Debye length $\lambda_D$ is not exceeded, and the aptamers can induce their negative charges to the extended gate electrode surface. As explained above, the final modified electrode is electrically connected to the gate of the sensing MOSFET, which may be fabricated in a 0.18 μm CMOS process.

The use of aptamers as catch probes, which is the solution adopted in the present invention, has some clear attractive advantages over some other possible catch probes. Aptamers are single-stranded nucleic acid molecules, which are negatively charged due to the presence of a phosphate group in each nucleotide of the nucleic acid strand. Aptamers can fold into three-dimensional topologies, with specifically designed pockets for binding with a target of interest. Compared to antibodies, aptamers have superior advantages as catch probes as they are synthesised in vitro, reducing the batch-to-batch difference. Additionally, they can be designed for different degrees of affinity for a targeted molecule versus a modified disturbing analogue. Moreover, aptamers are less affected by temperature fluctuations and are more stable for long term storage. They can be covalently immobilised on most surfaces by modifying the 5' or 3' end. The aptamers that can be used to detect cortisol levels have 40, 61 and 85 nucleotides. The one with 85 nucleotides when applied to a FET sensor would have a detection limit of 50 nM. However, for a FET sensor facing the challenge of the Debye length, the shorter length of the aptamer is expected to have better sensitivity and lower detection limit as it has higher chance to not exceed the Debye length when it reacts with the target. The working mechanism of the proposed sensor 1 and its figures of merit are described next in more detail. Our charge detection hypothesis is that the negatively charged aptamers 25 approach the conductive electrode surface within the Debye length, due to the folding phenomenon, which arises from the binding of the cortisol 51 to the aptamers 25. This binding event causes the strands to fold on themselves, and they come closer to the electrode surface. Consequently, the surface potential ψ of the electrode 21 is modulated by the cortisol concentration in the solution 27. Due to the relation existing between the threshold voltage $V_T$, and the surface potential ψ at the interface between the solution 27 and the sensing film (i.e. the graphene layer), any change in the cortisol concentration C induces a change in $V_T$ of the EGFET sensor 1:

$$V_{T\ EGFET} = V_{T\ FET} - \frac{\phi_M}{q} + E_{REF} + \chi^{Sol} - \psi(C), \quad (1)$$

where the $V_{T\ FET}$ is the threshold voltage of the MOSFET 3, $\phi_M$ is the work function of the metal gate, i.e., the sensing electrode 21, and relative to the vacuum, $E_{REF}$ is the potential of the reference electrode 29, and $\chi^{Sol}$ is the surface dipole potential of the solution 27. Therefore, at a voltage applied to the external gate, the surface potential ψ is modified by the number of negative charges induced by the folded aptamers 25, which results in a right shift of the $I_{DS}$-$V_{REF}$ curves of a n-channel MOSFET.

It is worth noting that the electrical dipole χ at the interface between the metal gate (i.e. the sensing electrode 21) and the solution 27 and the potential across the electrochemical double layer, which are charge layers, are the two phenomena that modulate the gate potential across the MOS. The value of χ is influenced by different microscopic phenomena, such as the distribution of charges in the immobilised chemical species, and the ionic physisorption and chemisorption exchange between the modified gate and the solution 27. As a result, the threshold voltage can be affected and hence deteriorate the sensitivity of an EGFET. In addition, the sensitive recognition of small molecules at low concentrations using the FET sensors may have particular challenges related to screening and size effects. Sensitive detection of small molecules at low concentrations by carbon nanotubes (CNTs) or by a graphene-based FET method is challenging due to the reduced electric field-effect of small size and few charge analytes and is even more difficult for uncharged analytes.

In order to validate the operation of the proposed device architecture for cortisol sensing and to extract its sensitivity, the sensor response to different cortisol concentrations in a buffer solution has been experimentally investigated. For this purpose, the transfer characteristics, $I_{DS}$-$V_{REF}$, of the EGFET transducer with different cortisol concentrations in prepared buffer solutions, ranging between 1 nM and 10 µM (corresponding to cortisol concentrations in human biofluids, such as plasma and sweat), have been systematically recorded at low drain voltage (100 mV), ensuring linear region operation. The goal is to achieve a high sensitivity in the whole range of cortisol concentrations (over four orders of magnitude) with a lower limit in the nM range. Therefore, the response of the EGFET sensor has been studied in different regimes of the inversion channel charge: (i) the weak inversion region (where $V_{REF}$ is smaller than $V_T$, and the current is given by a diffusion mechanism), and (ii) the strong inversion region of operation (when $V_{REF}$ is greater than $V_T$, and the current is given by a drift mechanism).

Figure 5:
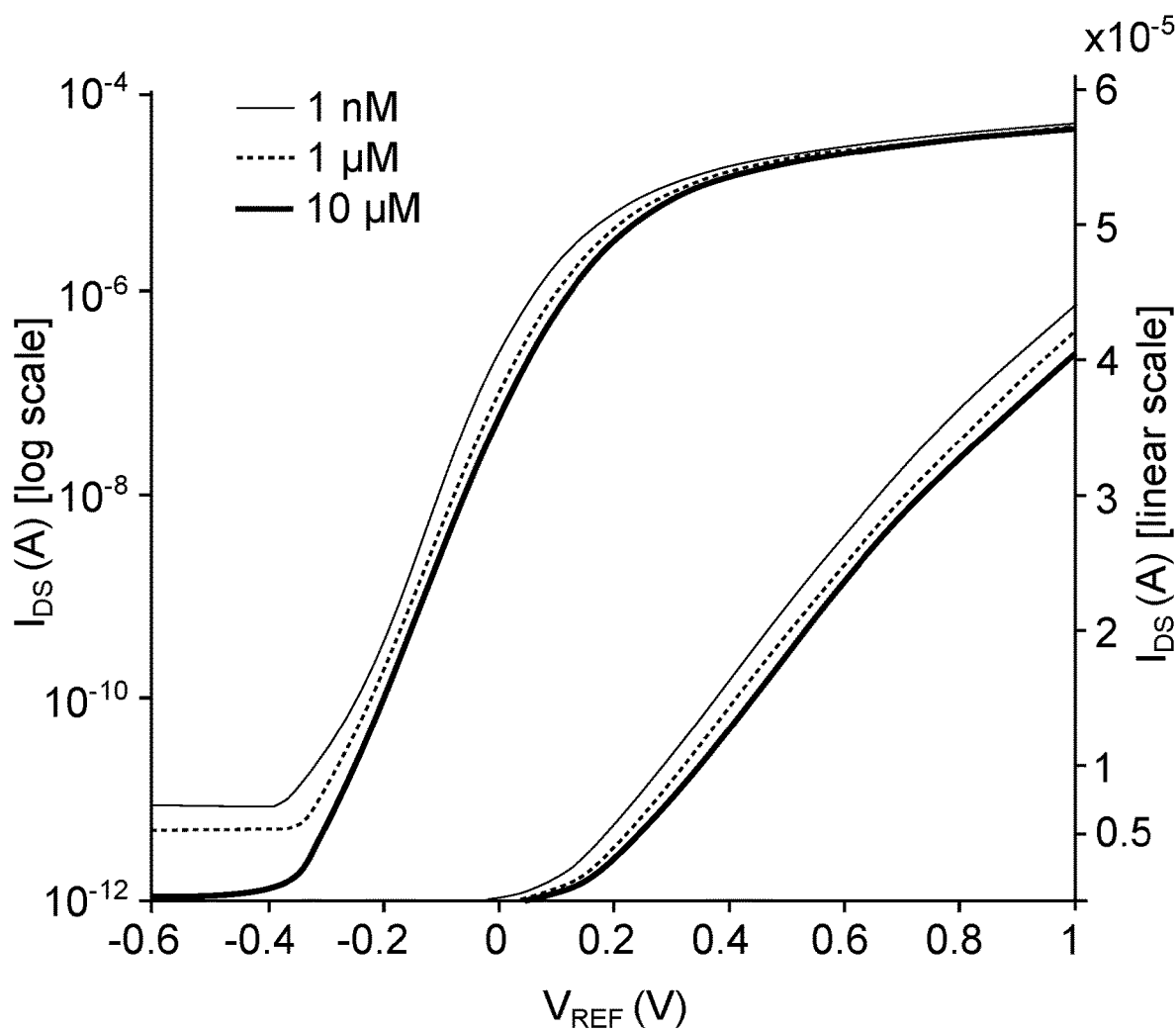
FIG. 5 shows how the "drain current-reference voltage" curves shift depending on the cortisol concentration in the sensed solution.

It is well established that the modulation of the conductance of the FET-based sensors upon binding of the target is correlated with the concentration when the gate and drain voltages are fixed. As illustrated in FIG. 5, after incubation of the different cortisol concentrations, the $I_{DS}$-$V_{REF}$ curves shift to the right direction as the cortisol concentration increases. A notable achievement of the proposed sensor functionalisation is that the $I_{DS}$-$V_{REF}$ curves show a negligible hysteresis, typically lower than 4 mV, and a small variation between repeated measurement with the same cortisol concentration. The extraction of the voltage shifts is performed at constant current both in the subthreshold operation regime ($V_{REF}$<$V_T$) and in the strong inversion operation regime ($V_{REF}$>$V_T$) within a wide range of cortisol concentrations, from 1 nM and 10 µM.

Two types of sensitivities are extracted to evaluate the figures of merit of the sensor 1: (i) a voltage sensitivity, $$S_V = \frac{dv_{REF}}{d\log_{10}(Conc)}\bigg|_{I_D=const},$$

corresponding to the variation of the applied reference voltage to obtain the same drain current for different cortisol concentrations, and, (ii) a current sensitivity, $$S_I = 100x\frac{\Delta I}{I_0} = 100x\frac{|I_i - I_0|}{I_0},$$

where $I_i$ is the current value at fixed gate voltage for a given concentration, and $I_0$ is the current at a baseline lower concentration (serving as a refence value).

In the subthreshold regime, $S_V$ ranges between 11.9 mV/decade and 14.7 mV/decade for different constant drain current levels, with the higher value measured for $I_{DS}$=1 nA, while in strong inversion, it varies from 12.4 mV/decade to 14.0 mV/decade. The proposed FET sensor 1 shows similar voltage sensitivity for both working regimes, with a stable $S_V$ and excellent linearity for detecting cortisol over four decades of concentration, demonstrating the full sensing capability of the designed aptamer-based catch mechanism. The LOD of the sensor in this example is 0.2 nM. The value of LOD depends on the sensitivity of the sensor. As previously explained, the sensitivity is limited by the additional phenomena affecting the value of $\chi$. Moreover, it is reported that a graphene surface has a tendency to attract some biological molecules. Therefore, a high concentration of the aptamers, e.g. 50 µM to 200 µM, and more specifically approximately 100 µM, is used for the functionalisation of the electrode 21 to cover the surface of the graphene 23 by aptamers as densely as possible and to minimise the free graphene spaces, and therefore to decrease any unspecific attachment of the molecules on the surface of the graphene 23. However, it should be noted that a too dense population of the aptamers 25 on the surface of the graphene 23 may restrict them to bend freely after attachment to the cortisol 51 as a result of space disturbance by the neighbouring aptamers. This phenomenon creates a trade-off, and it limits the sensitivity of this sensor and the corresponding LOD.

A noticeable difference in the performances of the sensor 1 in the two regimes is obtained for $S_I$, due to the exponential dependence between the subthreshold drain current and the threshold voltage in the weak inversion regime, compared to the strong inversion regime where the current depends quasi-linearly on the threshold voltage. While the relative current change reaches values near 80% for the highest cortisol concentration in the subthreshold regime, it is limited to about 20% in the strong inversion regime. Such exponential dependence in the weak inversion regime plays an important role considering the relative current changes for different concentrations, opening the path to a higher sensor resolution in this regime.

In order to analyse the sensor response in all the working regimes of the FET for the whole cortisol concentration range in human biofluids, a compact physical sensor model was developed. The drain current is modelled with the following unified equation that accurately describes, the weak, moderate and strong inversion regions of a long channel MOSFET:

$$I_D(V_{GS}) = \eta U_T^2 K_n \ln\left(e^{\frac{V_{GS}-V_T}{\eta U_T}} + 1\right)\left(1 - e^{\frac{-V_{DS}}{U_T}}\right), \quad (2)$$

where $\eta = \delta V_{GS}/\delta \psi_S$ is the transistor body factor ($=1+C_{ox}/C_{dep}$>1), $U_T$=kT/q is the thermal voltage, $$K_n = \frac{W}{L}\mu_0 C_{ox},$$

W/L is the channel width over length ratio, $\mu_0$ is the low-field mobility, and $C_{ox}$ and $C_{dep}$, are the gate oxide and depletion capacitance, respectively. The experimental $I_{DS}$-$V_{REF}$ curves at a given cortisol concentration are excellently approximated over the whole range of operation by this model. Equation 2 is uniquely adapted to investigate a FET sensor, as it captures the role of threshold voltage, body factor and temperature in a single unified equation, which can be simplified into traditional equations per regimes of operation. By combining Equation 2 with the threshold voltage dependence on analyte concentration, we derive a closed non-linear logarithmic expression of the dependence of the FET sensor current $I_{DS}$ on the cortisol concentration C for every sensor bias point:

$$I_D(V_{GS}) = \eta U_T^2 K_n \ln\left(1 + \left(\frac{c}{c_{ref}}\right)^{-\frac{m}{\eta U_T}} e^{\frac{V_{GS}-V_T}{\eta U_T}}\right)\left(1 - e^{\frac{-V_{DS}}{U_T}}\right), \quad (3)$$

where m is a non-ideality factor that characterises the sensor efficiency and could potentially capture specific Langmuir adsorption surface phenomena, while $C_{ref}$ is the lowest concentration (1 nM) investigated in the reported series of experiments, taken as a normalising reference. It is to be noted that Equation 2 is valid in all the operation regions of the sensor, and it is believed to be the first unified analytical expression capable of precisely predicting FET sensor response to the cortisol, to analytically capture the sensing performance and optimise the signal-to-noise ratio and power consumption.

Finally, two other important figures of merit of the proposed cortisol sensor 1 have been studied and reported here: (i) the sensor selectivity, which describes the specificity of the sensor towards the target in the presence of interfering compounds, and, (ii) the drift of the response caused by the environmental effects over time. They are both important for designing an accurate sensor and for employing it to produce high quality reliable data in practice. In order to study the selectivity, we investigated the effect of the testosterone hormone, another adrenal hormone with similar structure to the cortisol, and cortisone, a metabolised form of cortisol in the peripheral tissue. The proposed sensor was exposed to different controlled concentrations of the testosterone in the range of human biofluids and cortisone in the range of concentrations similar to the cortisol measurement. Then the transfer characteristics of the EGFET were recorded. No significant trend was observed for $I_{DS}$-$V_{REF}$ curves as the testosterone or cortisone concentration increases, which validates the high selectivity of our aptamer functionalisation. In addition, the drift in the response of the sensor 1 was investigated by immersing the sensor into an incubation buffer for 30 minutes for three consecutive times and by recording the sensor response. No significant trend in the $I_{DS}$-$V_{REF}$ curves was observed after 1.5 hours, which demonstrates that the proposed cortisol sensor 1 based on aptamer functionalisation has a very stable, drift-independent response.

Figure 6:
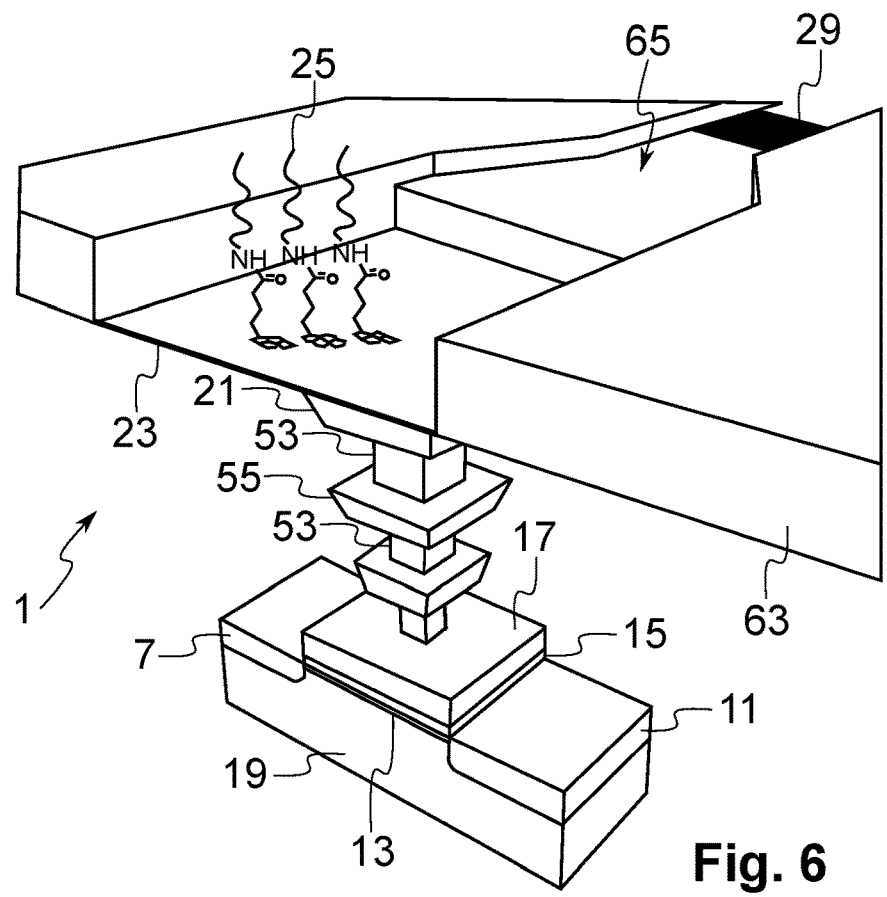
FIG. 6 is a perspective view of a system-on-chip configuration of the proposed biosensor according to a second embodiment of the present invention.
Figure 7:
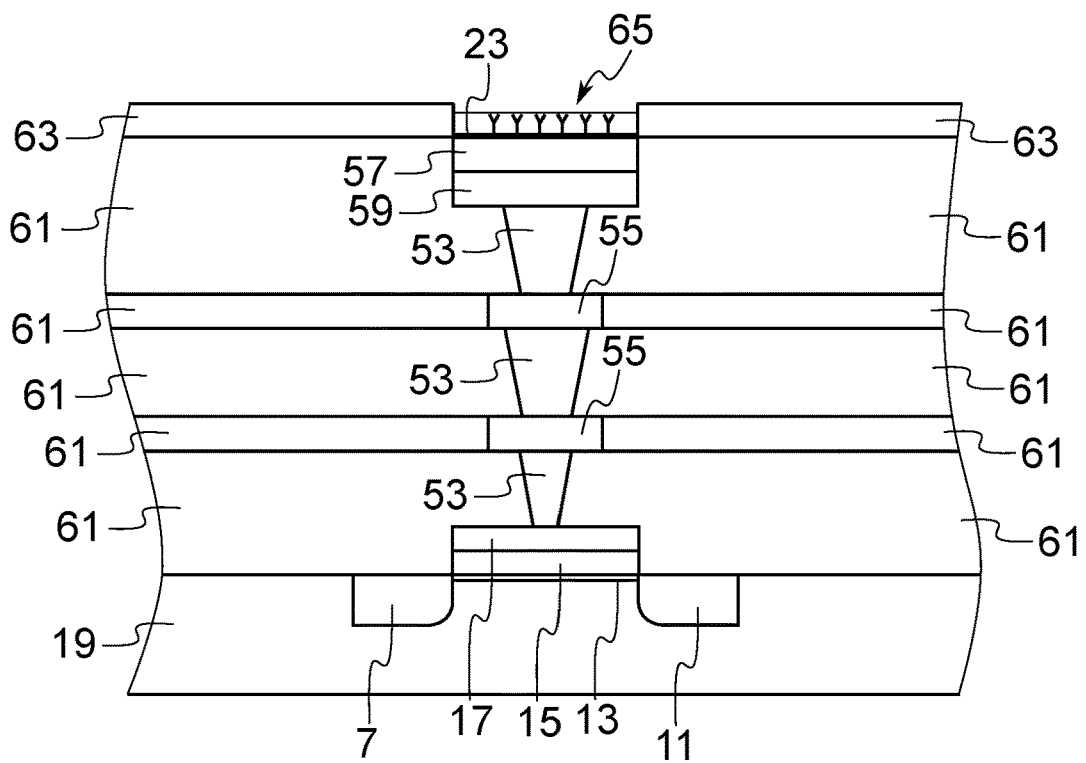
FIG. 7 is a schematic cross-sectional view of the configuration of FIG. 6.
Figure 8:
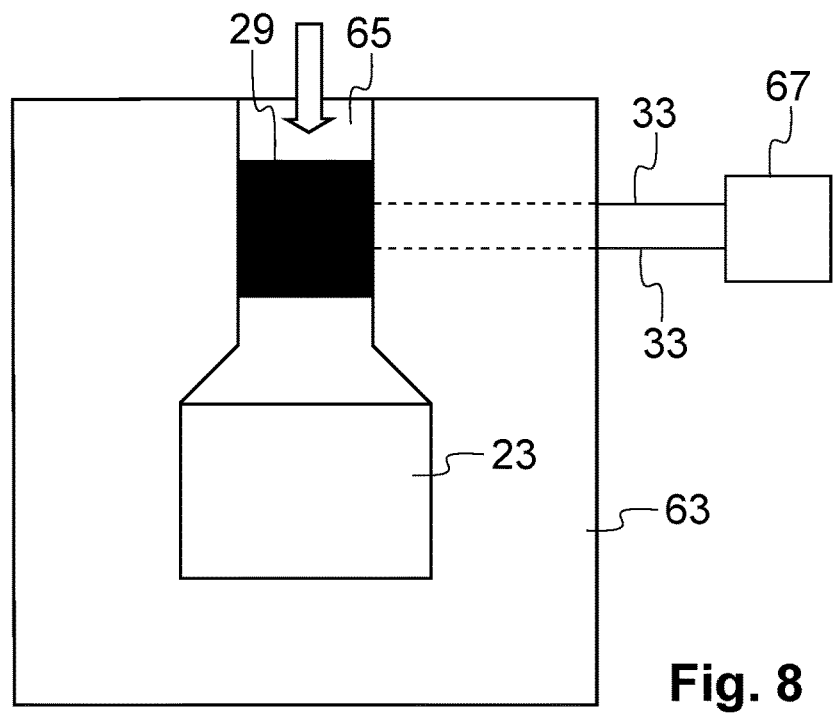
FIG. 8 is a schematic top view of the configuration of FIG. 6.

FIGS. 6 to 8 illustrate a system-on-chip or a sensor-on-chip configuration according to the second embodiment of the present invention. The above teachings are thus in this embodiment applied in a sensor-on-chip system. FIG. 6 shows the configuration in a schematic perspective view, FIG. 7 is a cross-sectional view, and FIG. 8 is a top view of the sensor-on-chip configuration. As can be seen in the figures, the configuration comprises a fully 3D-integrated reference electrode 29 on top of an electronic silicon chip. The transducer gate electrode 17 is connected to the sensing electrode 21 by an electrically conductive structure forming an electrical connector comprising an alternating arrangement of electrically conductive vias 53 and other conductive elements 55 as shown in FIGS. 6 and 7. The sensing electrode 21 in this example comprises a first electrically conductive element 57 and a second electrically conductive element 59. In this example, the first conductive element 57 is a platinum element which may thus be substantially identical to the platinum plate 45 used in the configuration of FIG. 1. However, the glass layer is replaced in the present embodiment with a metal plate, where the metal may be one of aluminium, aluminium-copper alloy, and copper. The conductive elements 55 may also be made of one of aluminium, aluminium-copper alloy, and copper. The electrically conductive structure may thus be understood to form an electrically conductive wire or electrical connector between the sensing electrode 21 and the transducer gate electrode 17. The electrically conductive structure is laterally fully or substantially fully encompassed or surrounded by an insulating element or dielectric 61 along the entire length or substantially entire length of the electrical connector. The insulating element may thus be called a lateral insulator. The insulating element is a low permittivity dielectric, such as a silicon oxide. The lateral insulators are omitted in FIG. 6 for illustration purposes. Furthermore, the electrical connectors to the drain and source elements are also omitted in the figures.

The electronic chip further comprises in its top part a microfluidic channel element 63 comprising one or more microfluidic channels 65, where also the sensing region is located. A microfluidic channel is understood to mean a hollowed-out space in the microfluidic channel element 63, and which has its cross-sectional dimension (when the cross section is taken orthogonally to the longitudinal axis of the channel) from tens to hundreds of micrometres, or more specifically between 10 micrometres and 500 micrometres. The sensing region comprises the functionalisation layer as described above. A reference electrode is also provided in the microfluidic channel as shown in FIG. 8. The solution 27 to be sensed flows into the sensing region according to the direction of the arrow shown in FIG. 8. The reference electrode is connected to a metal pad 67 through one or more electrical connectors 33 for applying $V_{REF}$ (=$V_G$) to the reference electrode 29. Here it is to be noted that the drawings are not drawn to scale, and for instance the metal pad 67 may be located far away from the reference electrode 29. The configuration of FIGS. 6 to 8 may thus be used as a patch on a skin to measure the cortisol concentration in biofluids by following the principles explained above. The proposed configuration is particularly advantageous as it includes an integrated transistor transducer together with an integrated reference electrode, which is preferably placed in the microfluidic channel, and is advantageously in this example a thin plate-like element.

Figure 9:
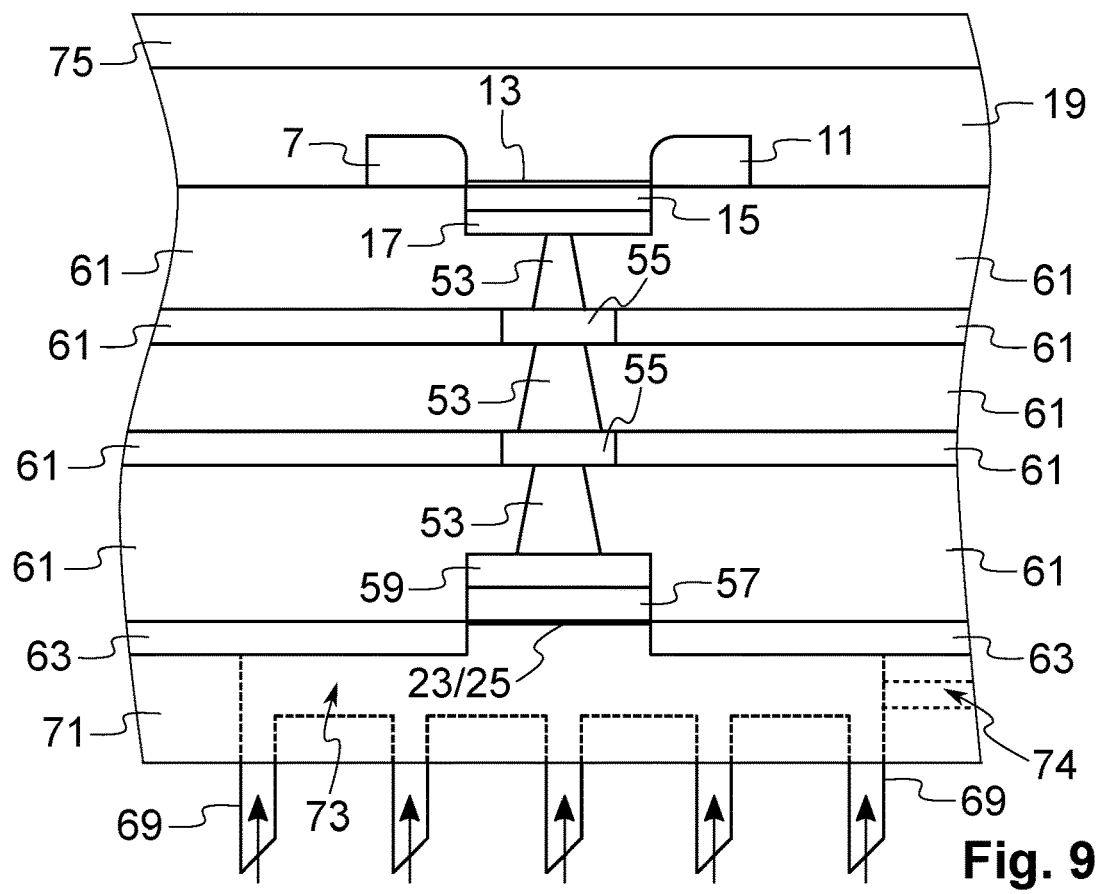
FIG. 9 is a schematic cross-sectional view of a system-on-chip configuration of the proposed biosensor according to a third embodiment of the present invention.

FIG. 9 schematically illustrates in a cross-sectional view the third embodiment of the present invention. As can be seen, the configuration of FIG. 9 is somewhat similar to the configuration of FIGS. 6 to 8. More specifically, the arrangement of FIG. 9 is also a system-on-chip or a sensor-on-chip configuration. However, the main difference between the configuration of FIG. 9 and the configuration of FIGS. 6 to 8 is the fact that the configuration of FIG. 9 comprises an array of needles 69 for collecting and guiding fluids, and more specifically interstitial fluids, to the sensing region of the sensor 1. The needles are thus configured to penetrate at least the topmost skin layer, i.e., the epidermis, but optionally without piercing any blood veins. The length of the needles may thus be designed so that they are only configured to pierce the topmost skin layer. The array of needles comprises one or more needles, and typically between 5 and 500 needles, or more specifically between 10 and 300 needles or between 50 and 250 needles. The needles are received in a skin interface element 71, which is placed directly or indirectly on the skin, when the sensor 1 is in use. The skin interface element 71 is made of any suitable biocompatible material, such as any suitable polymer, silicon, or metal. When the sensor 1 is in use, the fluids flow through the hollow needles thanks to the capillary effect to an internal (fluid) cavity 73 within the skin interface element, which in turn faces the sensing region comprising the functionalised sensing electrode 21, such that the internal cavity 73 is in fluid communication with the sensing region. The fluid flow direction is illustrated by the arrows in FIG. 9.

A microfluidic interposer may optionally be placed between the skin interface element 71 and the microfluidic channel element 63 to hermetically seal the microfluidic channel element 63. Furthermore, as shown in FIG. 9, there may be a flexible substrate 75 on the substrate 19. It is to be noted that FIG. 9 omits electrical connectors to the drain and source elements. The elements in FIG. 9 apart from the flexible substrate 19, the needles 69, the skin interface element 71 and the microfluidic interposer may be considered to form an electronic chip. The sensory system of FIG. 9 may be summarised as a sensor-on-chip system integrated as described above, and placed inside or on top of an array of needles that exploits microfluidics to collect and drain an external biofluid and uses microfluidic channels to wet the functionalised electrode in order to finally sense the cortisol concentration in the collected biofluid.

FIG. 9 also shows another microfluidic channel 74, which is an optional feature, and which is useful in the case where the sensing of the collected interstitial fluid is done continuously or substantially continuously. In this case, this channel is advantageously connected through the skin interface element 71 to an external adsorbent layer or to a micropump that would extract at a given flow rate the collected fluid in order to allow the liquid under test to be renewed, and to allow the cortisol concentration of a new solution sample to be measured. This kind of channel would thus form a fluid evacuation channel to remove the fluid or at least some of it from the internal cavity 73 through the channel 74. With a size of the fluid cavity 73 of the order of 1 micro litre or less, such an arrangement would have the capability to renew the collected interstitial fluid and repeat an experimental measurement a few times per hour, for example. It is to be noted that the above channel arrangement could also be integrated to the configuration shown in FIGS. 6 to 8 to take continuous measurements. Furthermore, more than one fluid evacuation channel may be provided.

To summarise the above teachings, the present invention proposes a new design for an EGFET sensor 1 for selective recognition or sensing of cortisol hormones (or other hormones) by exploiting a single layer of graphene on a metal layer, and aptamers as the gate electrode and catch probes, respectively. The utilisation of the aptamers as the recognition elements make the proposed sensor highly sensitive, selective and stable. The proposed EGFET 1 is hysteresis-free and showed unique sub-nanomolar detection limit, negligible drift, and high selectivity over a wide dynamic range of concentrations. Its dynamic range and low detection limit make it a promising candidate for the detection of normal and abnormal amount of the cortisol in biofluids, such as sweat, saliva and serum. A compact model for the drain current, i.e., the sensor output current, in all regimes of operations, useful for sensor optimised design, was proposed and validated. This enabled the derivation of the first analytical expression of the sensor output current as a function of the cortisol concentration with high predictive capability. These features make this sensor an excellent candidate for integrated miniaturised lab-on-chip or lab-on-skin wearable sensory systems capable of monitoring the concentration of cortisol in human or animal biofluids.

While the invention has been illustrated and described in detail in the drawings and foregoing description, such illustration and description are to be considered illustrative or exemplary and not restrictive, the invention being not limited to the disclosed embodiments. Other embodiments and variants are understood, and can be achieved by those skilled in the art when carrying out the claimed invention, based on a study of the drawings, the disclosure and the appended claims. Further embodiments may be obtained by combining any of the teachings above.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used.

The invention claimed is:

1. A cortisol biosensor for sensing cortisol concentration in a biofluid, the biosensor comprising:
an electrical transistor transducer comprising a transistor gate electrode;
a sensing electrode element comprising a metal element having a biofluid facing surface, and a single graphene layer on the biofluid facing surface of the metal element thereby forming a monolayer graphene sheet on the metal element, the sensing electrode element being connected to the transistor gate electrode by an electrical connector to form an extended gate configuration with the transistor gate electrode;
a reference electrode configured to be immersed in, or in contact with the biofluid, and configured to electrically bias the transistor gate electrode through the biofluid,
wherein the sensing electrode element is functionalised by at least a layer of aptamers placed indirectly or directly on the single graphene layer, and configured to catch cortisol hormones in the biofluid to thereby change a surface potential of the sensing electrode element.

2. The biosensor according to claim 1, wherein the single graphene layer defines a sensing region, wherein the biosensor comprises a microfluidic channel, and wherein the sensing region and/or the reference electrode is/are in the microfluidic channel.

3. The biosensor according to claim 2, wherein the microfluidic channel is formed in a microfluidic channel element, wherein the microfluidic channel is a hollowed-out space in the microfluidic channel element, and wherein the microfluidic channel has a cross-sectional diameter orthogonally to a longitudinal axis of the microfluidic channel between 10 micrometres and 500 micrometres.

4. The biosensor according to claim 1, wherein the metal element is a platinum element.

5. The biosensor according to claim 1, wherein the aptamers have a proximal end attached directly or indirectly to the single graphene layer, and an opposite distal end away from the single graphene layer, and wherein the distal ends of the aptamers are within a Debye limit of detection of the single graphene layer.

6. The biosensor according to claim 5, wherein the distal ends of the aptamers are within 0.7 nm to 7.4 nm of the single graphene layer.

7. The biosensor according to claim 1, wherein the biosensor further comprises a set of linker molecules placed between the single graphene layer and the aptamers for attaching the aptamers to the linker molecules.

8. The biosensor according to claim 7, wherein the linker molecules are 1-Pyrenebutyric acid N-hydroxysuccinimide ester molecules.

9. The biosensor according to claim 1, wherein the reference electrode is a plate-like element, and wherein the electrical transistor transducer is placed under the sensing electrode element.

10. The biosensor according to claim 1, wherein the electrical connector is laterally encompassed by an electrical insulator along the length of the electrical connector.

11. The biosensor according to claim 1, wherein the biosensor comprises an array of hollow needles for collecting the biofluid and guiding the biofluid to the sensing electrode element.

12. The biosensor according to claim 11, wherein the biosensor comprises a skin interface element such that the array of the needles being at least partially received therein, and wherein the skin interface element comprises a cavity in fluid communication with the sensing electrode element.

13. The biosensor according to claim 1, wherein the biosensor further comprises a fluid evacuation channel for removing at least some of the biofluid away from a fluid sensing region defined by the single graphene layer and/or from a cavity of a skin interface element comprised by the biosensor.

14. The biosensor according to claim 1, wherein the electrical transistor transducer is a field-effect transistor or a tunnel field-effect transistor.

15. The biosensor according to claim 1, wherein the biosensor is a label-free sensor.

16. The biosensor according to claim 1, wherein the aptamers are 40-nucleotide-based, 61-nucleotide-based and/or 85-nucleotide-based aptamers.

17. A wearable lab-on-chip device comprising the biosensor according to claim 1.

18. A method of fabricating a cortisol biosensor for sensing cortisol hormone concentration in a biofluid, the method comprising:
 depositing a single layer of graphene on a first layer of metal;
 coating the single layer of graphene with a layer or thermoplastic;
 removing the first layer or metal;
 transferring the single layer of graphene together with the layer of thermoplastic onto a second layer of metal;
 removing the layer of thermoplastic thereby forming a monolayer graphene sheet on the second layer of metal;
 functionalising the single layer of graphene with a layer of aptamers to form a functionalised sensing electrode element;
 connecting the sensing electrode element to a transistor gate electrode of an electrical transistor transducer by an electrical connector to form an extended gate configuration with the transistor gate electrode; and
 adding a reference electrode configured to be immersed in, or in contact with the biofluid, and configured to electrically bias the transistor gate electrode through the biofluid.

* * * * *